United States Patent
Agamaite

(10) Patent No.: US 9,757,591 B2
(45) Date of Patent: Sep. 12, 2017

(54) METHODS AND SYSTEMS FOR MONITORING AN AUTOMATED INFUSION SYSTEM

(71) Applicant: MEDRAD, INC., Indianola, PA (US)

(72) Inventor: James A. Agamaite, Wexford, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 234 days.

(21) Appl. No.: 13/764,426

(22) Filed: Feb. 11, 2013

(65) Prior Publication Data
US 2014/0228617 A1    Aug. 14, 2014

(51) Int. Cl.
*A61M 36/04* (2006.01)
*A61N 5/10* (2006.01)
(Continued)

(52) U.S. Cl.
CPC ........... *A61N 5/1075* (2013.01); *A61M 5/007* (2013.01); *A61M 5/14* (2013.01); *A61M 5/16831* (2013.01); *A61N 5/1007* (2013.01); *G06F 19/3468* (2013.01); *A61M 5/1785* (2013.01); *A61M 2005/1588* (2013.01); *A61M 2202/049* (2013.01); *A61M 2205/15* (2013.01); *A61M 2205/18* (2013.01); *A61M 2205/3306* (2013.01); *A61M 2205/3317* (2013.01); *A61M 2205/3327* (2013.01); *A61M 2205/3331* (2013.01);
(Continued)

(58) Field of Classification Search
CPC .............................................. A61N 2005/1021
USPC ......................................................... 600/1–8
See application file for complete search history.

(56) References Cited

U.S. PATENT DOCUMENTS 6,015,387 A    1/2000    Schwartz et al.
6,089,103 A    7/2000    Smith
(Continued)

FOREIGN PATENT DOCUMENTS

WO    0121057 A2    3/2001
WO    03022122 A2    3/2003
(Continued)

OTHER PUBLICATIONS

International Search Report and Written Opinion mailed on May 22, 2014 from corresponding PCT Application No. PCT/US2014/015732, filed Feb. 11, 2014.
(Continued)

*Primary Examiner* — Catherine B Kuhlman
(74) *Attorney, Agent, or Firm* — Joseph L. Kent; David Schramm; James R. Stevenson

(57) ABSTRACT

Methods and systems for monitoring an automated radiopharmaceutical infusion apparatus are disclosed. A user interface graphically representing infusion apparatus components may be presented on a display device. Multiple sensors may be arranged within an infusion apparatus to measure property information associated with infusion apparatus components, including fluid pathways. The property information may include radioactivity and flow information. The property information may be compared with expected results. If the property information does not match the expected results, a fault condition may be indicated on the display device. The user interface may provide information and/or functions to manage the fault conditions.

23 Claims, 4 Drawing Sheets

(51) Int. Cl.
  *A61M 5/14* (2006.01)
  *A61M 5/00* (2006.01)
  *A61M 5/168* (2006.01)
  *G06F 19/00* (2011.01)
  *A61M 5/158* (2006.01)
  *A61M 5/178* (2006.01)

(52) U.S. Cl.
  CPC .............. *A61M 2205/3334* (2013.01); *A61M 2205/3368* (2013.01); *A61M 2205/3375* (2013.01); *A61M 2205/3379* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01)

(56) References Cited

U.S. PATENT DOCUMENTS

| | | |
|---|---|---|
| 6,142,958 A | 11/2000 | Hammarstrom et al. |
| 6,193,669 B1 | 2/2001 | Degany et al. |
| 6,296,615 B1 | 10/2001 | Brockway et al. |
| 6,336,906 B1 | 1/2002 | Hammarström et al. |
| 6,343,514 B1 | 2/2002 | Smith |
| 6,354,999 B1 | 3/2002 | Dgany et al. |
| 6,409,677 B1 | 6/2002 | Tulkki |
| 6,471,656 B1 | 10/2002 | Shalman et al. |
| 6,558,334 B2 | 5/2003 | Shalman et al. |
| 6,565,514 B2 | 5/2003 | Svanerudh et al. |
| 6,585,660 B2 | 7/2003 | Dorando et al. |
| 6,615,667 B2 | 9/2003 | Smith |
| 6,659,959 B2 | 12/2003 | Brockway et al. |
| 6,663,570 B2 | 12/2003 | Mott et al. |
| 6,663,571 B1 | 12/2003 | Njemanze |
| 6,672,172 B2 | 1/2004 | Tulkki et al. |
| 6,743,180 B1 | 6/2004 | Van Bockel |
| 6,754,608 B2 | 6/2004 | Svanerudh et al. |
| 6,855,115 B2 | 2/2005 | Fonseca et al. |
| 6,868,736 B2 | 3/2005 | Sawatari et al. |
| 6,895,265 B2 | 5/2005 | Silver |
| 6,959,608 B2 | 11/2005 | Bly et al. |
| 7,033,322 B2 | 4/2006 | Silver |
| 7,073,387 B2 | 7/2006 | Zdeblick et al. |
| 7,134,994 B2 | 11/2006 | Alpert et al. |
| 7,181,261 B2 | 2/2007 | Silver et al. |
| 7,274,956 B2 | 9/2007 | Mott et al. |
| RE39,863 E | 10/2007 | Smith |
| 7,284,441 B2 | 10/2007 | Zdeblick |
| 7,313,431 B2 | 12/2007 | Uber, III et al. |
| 7,398,688 B2 | 7/2008 | Zdeblick et al. |
| 7,415,883 B2 | 8/2008 | Kaplan |
| 7,454,244 B2 | 11/2008 | Kassab et al. |
| 7,481,771 B2 | 1/2009 | Fonseca et al. |
| 7,481,774 B2 | 1/2009 | Brockway et al. |
| 7,488,345 B2 | 2/2009 | Brown et al. |
| 7,549,977 B2 | 6/2009 | Schriver et al. |
| 7,563,249 B2 | 7/2009 | Schriver et al. |
| 7,677,107 B2 | 3/2010 | Nunez et al. |
| 7,713,232 B2 | 5/2010 | Uber, III et al. |
| 7,762,138 B2 | 7/2010 | Zdeblick et al. |
| 7,769,420 B2 | 8/2010 | Silver et al. |
| 7,775,988 B2 | 8/2010 | Pijls |
| 7,922,667 B2 | 4/2011 | Gianchandani et al. |
| 2002/0183628 A1 | 12/2002 | Reich et al. |
| 2003/0032886 A1 | 2/2003 | Dgany et al. |
| 2003/0191400 A1 | 10/2003 | Shalman et al. |
| 2004/0171983 A1* | 9/2004 | Sparks .............. A61M 5/16827 604/65 |
| 2004/0176699 A1 | 9/2004 | Walker et al. |
| 2006/0052700 A1 | 3/2006 | Svanerudh |
| 2006/0074318 A1 | 4/2006 | Ahmed et al. |
| 2006/0129050 A1 | 6/2006 | Martinson et al. |
| 2006/0149347 A1 | 7/2006 | Hayashi et al. |
| 2006/0200220 A1 | 9/2006 | Brown et al. |
| 2006/0241505 A1 | 10/2006 | Ahmed et al. |
| 2007/0060822 A1 | 3/2007 | Alpert et al. |
| 2007/0073271 A1 | 3/2007 | Brucker et al. |
| 2007/0255145 A1 | 11/2007 | Smith et al. |
| 2008/0033316 A1 | 2/2008 | Kassab et al. |
| 2008/0119741 A1 | 5/2008 | Friedman et al. |
| 2008/0131362 A1* | 6/2008 | Rousso .................. A61B 5/417 424/1.11 |
| 2008/0269572 A1 | 10/2008 | Kanz et al. |
| 2008/0281205 A1 | 11/2008 | Naghavi et al. |
| 2009/0082678 A1 | 3/2009 | Smith |
| 2009/0198308 A1 | 8/2009 | Gross et al. |
| 2009/0234231 A1 | 9/2009 | Knight et al. |
| 2009/0312635 A1 | 12/2009 | Shimchuk et al. |
| 2010/0109104 A1 | 5/2010 | Tiensuu et al. |
| 2010/0114040 A1 | 5/2010 | Schriver et al. |
| 2010/0234698 A1 | 9/2010 | Manstrom et al. |
| 2010/0241008 A1 | 9/2010 | Belleville et al. |
| 2010/0286537 A1 | 11/2010 | Pijls |
| 2010/0312039 A1* | 12/2010 | Quirico et al. .................... 600/4 |
| 2011/0066047 A1 | 3/2011 | Belleville et al. |
| 2011/0071404 A1 | 3/2011 | Schmitt et al. |
| 2011/0085977 A1 | 4/2011 | Rosenmeier |
| 2011/0178359 A1* | 7/2011 | Hirschman ............ A61B 6/037 600/4 |
| 2012/0220883 A1 | 8/2012 | Manstrom et al. |

FOREIGN PATENT DOCUMENTS

| | | |
|---|---|---|
| WO | 2005070299 A1 | 8/2005 |
| WO | 2010033971 A1 | 3/2010 |
| WO | 2011011346 A1 | 1/2011 |
| WO | 2011029569 | 3/2011 |
| WO | 2011153519 A2 | 12/2011 |
| WO | 2012151542 A2 | 11/2012 |
| WO | 2012155040 A1 | 11/2012 |

OTHER PUBLICATIONS

International Search Report and Written Opinion mailed Aug. 20, 2015 from corresponding PCT Application No. PCT/US2014/015732, filed Feb. 11, 2014.

"Extended European Search Report from EP14748626", Sep. 23. 2016.

* cited by examiner

METHODS AND SYSTEMS FOR MONITORING AN AUTOMATED INFUSION SYSTEM

BACKGROUND

Radiopharmaceuticals are radioactive drugs or contrast agents used to treat disease and diagnose medical problems. They may be administered to patients using various methods, such as orally or by injection. Certain procedures, such as positron emission tomography (PET), use automated infusion systems to deliver carefully measured doses of the radiopharmaceutical to patients. Maintenance and proper operation of infusion systems are critical to ensure the safe and efficient injection of each dose. In addition, medical personnel who routinely work with these systems must be protected from prolonged exposure to radiation from the radiopharmaceutical.

Conventional infusion systems do not provide adequate information regarding system components during the infusion process, particularly the multiple fluid channels used to move the radiopharmaceutical and other fluids throughout the infusion system. Consequently, it is difficult for medical personnel to know the status of internal components in real-time and to observe them without being exposed to radiation.

SUMMARY

The invention described in this document is not limited to the particular systems, methodologies or protocols described, as these may vary. The terminology used herein is for the purpose of describing particular embodiments only, and is not intended to limit the scope of the present disclosure.

It must be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. As used herein, the term "comprising" means "including, but not limited to."

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The property information may comprise fluid flow information.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The property information may comprise information indicating the presence of a fluid in a fluid pathway.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The apparatus components may comprise at least one fluid pathway.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The apparatus components may comprise a radiopharmaceutical source.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The apparatus component may comprise a dose meter In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The apparatus components may comprise a dispensing element.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The fault condition may comprise a flow rate below a threshold value.

In an embodiment, a system for monitoring an automated radiopharmaceutical infusion apparatus may comprise a plurality of fluid pathways and a plurality of sensors positioned to measure at least one property associated with the plurality of fluid pathways. At least one of the plurality of fluid pathways may comprise a radiopharmaceutical source pathway, and the at least one property may comprise radioactivity. The system may further comprise a display device, a processor in communication with the plurality of sensors and the display device, and a non-transitory, computer-readable storage medium in operable communication with the processor. The computer-readable storage medium may contain one or more programming instructions that, when executed, cause the processor to receive property information from the plurality of sensors, present an apparatus display graphically representing apparatus components based on the property information on the display device, compare the property information with expected results, generate a fault condition responsive to property information not matching expected results, and graphically represent the fault condition on the apparatus display. The apparatus components may comprise a directional valve configured to connect at least two of the plurality of fluid pathways. The fault condition may comprise the presence of fluid in a dry pathway.

In an embodiment, a method for monitoring an automated radiopharmaceutical infusion apparatus may comprise providing a plurality of sensors, providing a processor operatively connected to the plurality of sensors and a display device, and causing the processor to enable monitoring of the automated radiopharmaceutical infusion apparatus. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The processor may present information associated with the selected graphically represented fault condition.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. Comparing the property information with expected results may comprises determining, by the processor, a stage of an infusion process and comparing the property information with expected results for the stage of the infusion process. The stage of the infusion process may comprise a dry tubing priming stage.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. Comparing the property information with expected results may comprises determining, by the processor, a stage of an infusion process and comparing the property information with expected results for the stage of the infusion process. The stage of the infusion process may comprise a patient infusion stage.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The plurality of fluid pathways may further comprise at least one of the following: a saline pathway, a dose meter inlet pathway, a dose meter outlet pathway, and a waste pathway.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The plurality of radioactivity sensors may further comprise at least one of a silicon diode, a silicon PIN diode, an avalanche diode, a scintillator, a photomultiplier, a solid state crystal, a semiconductor, Geiger tubes, an ionization-chamber, a silicon photodiode, a microdischarge-based sensor, a sodium iodide crystal sensor, a bismuth tri-iodide crystal sensor, a cadmium tellurium crystal semiconductor, a cadmium zinc tellurium semiconductor, and combinations thereof.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The property information may comprise fluid flow information.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The property information may comprise information indicating the presence of a fluid in a fluid pathway.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The apparatus components may comprise a radiopharmaceutical source.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The apparatus components may comprise a dose meter.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The apparatus components may comprise a dispensing element.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The method may further comprise changing, by the processor, the position of the directional valve responsive to user input received by the processor.

In an embodiment, a method for monitoring an automated radiopharmaceutical infusion apparatus may comprise providing a plurality of sensors, providing a processor operatively connected to the plurality of sensors and a display device, and monitoring the automated radiopharmaceutical infusion apparatus using the processor. The plurality of sensors may be positioned to measure at least one property associated with the plurality of fluid pathways. The plurality of pathways may comprise at least one radiopharmaceutical fluid pathway, and the at least one property may comprise radioactivity. The processor may monitor the automated radiopharmaceutical infusion apparatus by receiving property information from the plurality of sensors, presenting an apparatus display graphically representing apparatus components based on the property information on the display device, comparing the property information with expected results, generating a fault condition responsive to property information not matching expected results, and graphically representing the fault condition on the apparatus display. The fault condition may comprise the presence of fluid in a dry pathway.

DETAILED DESCRIPTION

The terminology used in the description is for the purpose of describing the particular versions or embodiments only, and is not intended to limit the scope.

The present disclosure is directed toward obtaining and presenting information associated with the operation of an automated infusion apparatus, and a system configured to inject a radiopharmaceutical in particular. In one embodiment, the information may be associated with the fluids delivered through the infusion apparatus and/or the fluid channels used to move the fluids within and outside of the infusion apparatus. The information may be obtained through one or more sensors positioned throughout the infusion apparatus. Illustrative and non-restrictive examples of sensors include radioactivity, flow and optical sensors. A processor may be configured to receive the information. The processor may be connected to a display device and may execute one or more software applications configured to present a graphical display of the infusion apparatus on the display device. The one or more software applications may also compare the information with expected values. In an embodiment, if the information is not within the range of an expected value, a fault condition may be generated and visually represented on the graphical display.

Figure 1:
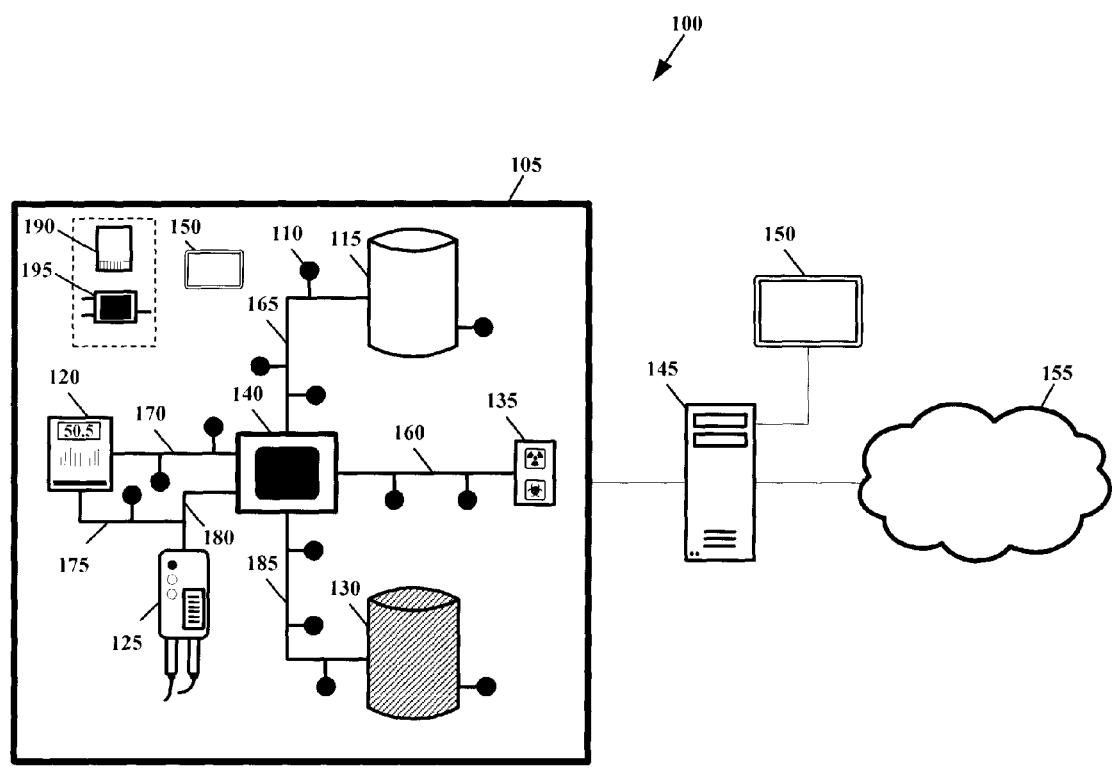
FIG. 1 depicts an illustrative automated infusion apparatus according to an embodiment.

FIG. 1 depicts an illustrative automated infusion apparatus according to an embodiment. As shown in FIG. 1, an automated infusion system 100 may include an infusion apparatus 105 configured to deliver a medical fluid to a patient. The infusion apparatus 105 may have a radiopharmaceutical bulk container 130 arranged therein and configured to hold a volume of the radiopharmaceutical in liquid or substantially liquid form. In a radiopharmaceutical infusion system, the radiopharmaceutical bulk container 130 may be in the form of a shielded vial, commonly referred to as a "pig," such as a lead or tungsten shielded vial. Other medical fluid containers 115 may also be positioned within the infusion apparatus 105. A non-limiting example of a medical fluid stored in the other medical containers 115 is saline, which may be used for various purposes known to those having ordinary skill in the art. For instance, saline may be used to dilute the radiopharmaceutical to a specified concentration, as a "chaser" to the radiopharmaceutical, to push the radiopharmaceutical through the automated infusion system 100, and combination thereof. A dose meter 120 may be provided that operates to verify the dose of the radiopharmaceutical that will be delivered to the patient through the dispensing element 125. The dose meter 120 may be comprised of various dose meters known to those having ordinary skill in the art, such as an ionization chamber. The dispensing element 125 may comprise any type of element capable of delivering the dose to the patient, such as intravenously through a syringe, catheter, needle, or automated injection system. A waste container 135 may be provided for receiving liquid waste within the system, such as excess saline or portions of the radiopharmaceutical outside of the radiopharmaceutical bulk container 130 after infusion is complete or has been stopped.

The infusion apparatus 105 includes multiple fluid pathways 160, 165, 170, 175, 180, 185 that allow various fluids to travel within the apparatus. The fluid pathways 160, 165, 170, 175, 180, 185 may include a flexible and deformable tube, such as a polyvinyl chloride (PVC) tube. In an embodiment, the fluid pathways 160, 165, 170, 175, 180, 185 may be comprised of generally disposable tubing that is replaced at various times, such as between infusions, daily, weekly, or when new radiopharmaceutical is placed in the infusion apparatus 105.

An infusion pump (not shown) may be used to pump the various fluids within the fluid pathways 160, 165, 170, 175, 180, 185. The fluid pathways 160, 165, 170, 175, 180, 185 may be connected to various valves and other components within the infusion apparatus. The fluid pathways 160, 165, 170, 175, 180, 185 may connect with a directional valve 140 configured to join one or more of the pathways in fluid communication. For example, the fluid pathway 165 for saline in the medical fluid container 115 may be joined with the fluid pathway 185 for the radiopharmaceutical, for instance, as a chaser and/or to dilute the radiopharmaceutical before delivery to the patient. The saline-radiopharmaceutical pathway 165, 185 may be joined with the inlet pathway 170 for the dose meter 120. The resulting saline-radiopharmaceutical-dose meter pathway 165, 185, 170 provides a channel for a dose of radiopharmaceutical to be measured by the dose meter 120. As shown in FIG. 1, the radiopharmaceutical may flow from the exit pathway 175 for the dose meter 120 to the pathway 180 for the dispensing element 125. The saline-radiopharmaceutical pathway 165, 185 may also be joined directly with the pathway 180 to the dispensing element 125. In this manner, two or more of the pathways 160, 165, 170, 175, 180, 185 may be joined in fluid communication and disconnected as needed during operation of the infusion apparatus 105.

One or more sensors 110 may be positioned within the infusion apparatus 105 to collect information associated with the apparatus pathways 160, 165, 170, 175, 180, 185 and apparatus elements 115, 130, 130. The sensors 110 may comprise any type of sensor capable of measuring a property of interest, including, without limitation, concentration, radioactivity, salinity, conductance, optical properties, analyte concentration, flow, and combinations thereof. Illustrative sensors 110 include, but are not limited to, temperature sensors, pressure sensors, radioactivity sensors, optical sensors, analyte sensors, concentration sensors, flow sensors, electro-resistive devices, electro-capacitive devices, ultrasound devices, and combinations thereof. For example, one or more sensors 110 may provide information concerning the volume of a medical fluid in a medical fluid container 115. In another example, one or more sensors 110 may provide information concerning the level of radioactivity associated with one or more of the pathways 160, 165, 170, 175, 180, 185. In a further example, one or more sensors 110 may provide information concerning the level of flow (e.g., cubic meters/second) of a fluid through one or more of the pathways 160, 165, 170, 175, 180, 185.

Figure 4:
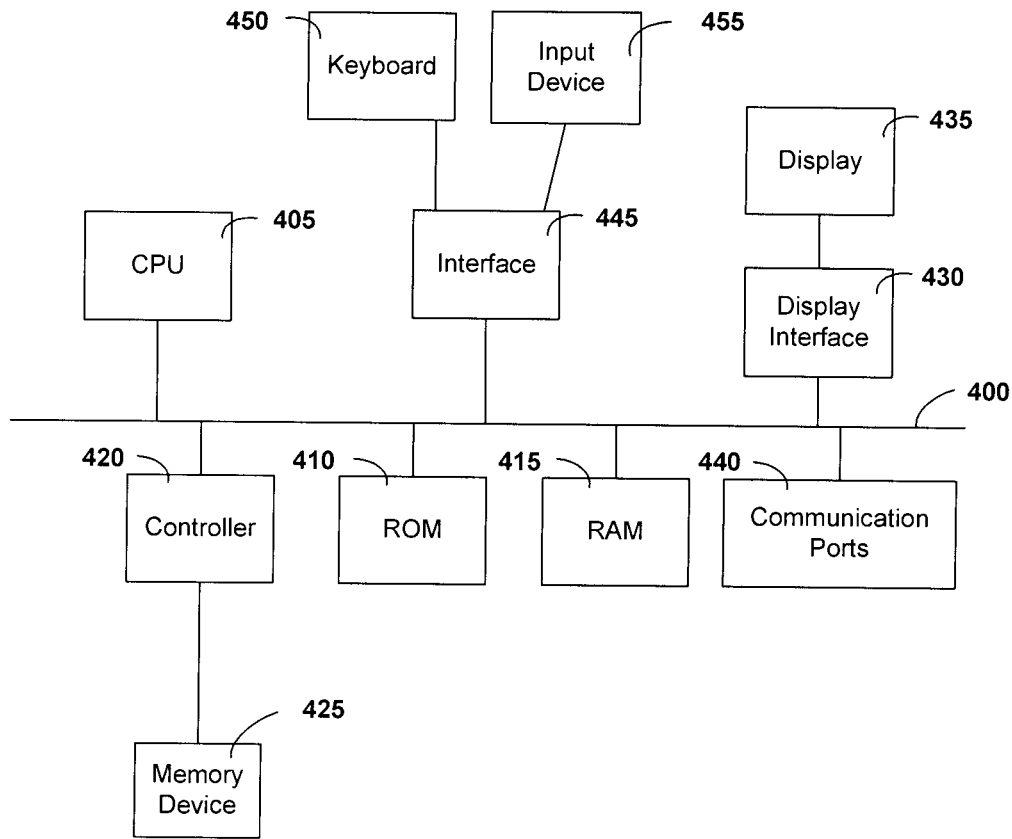
FIG. 4 depicts a block diagram of illustrative internal hardware that may be used to contain or implement program instructions according to an embodiment.

The infusion apparatus 105 may generally comprise one or more processors 195 and a non-transitory memory 190 or other storage device for storing programming instructions, one or more software programs (e.g., infusion apparatus control application) data or information regarding one or more applications, and other hardware, which may be the same or similar to the central processing unit (CPU) 405, read only memory (ROM) 410, random access memory 415, communication ports 440, controller 420, and/or memory device 425 depicted in FIG. 4 and described below in reference thereto.

The processors 195 may be in communication with various elements of the infusion apparatus 105, including, without limitation, the dispensing element 125, the dose meter 120, the directional valve 140, the radiopharmaceutical bulk container 130, the medical fluid containers 115, and sensors 110 arranged within the infusion apparatus and described in more detail below. The processors 195 may be in direct communication with the aforementioned elements or may be in communication with sensors 110 associated therewith. For example, for the radiopharmaceutical bulk container 130 and the medical fluid containers 115, the processors 195 may be in communication with sensors 110 configured to determine the remaining volume of fluids stored in the containers. In another example, the dose meter 120, directional valve 140, and dispensing element 125 may have internal elements (e.g., control circuits, transceivers, microprocessors, etc.) that may transmit/receive signals and information to/from the processor 195. For example, the processors 195 may transmit a signal to change the position of the directional valve 140.

The processors 195 may execute one or more software programs, such as an infusion apparatus control application, for operating the infusion apparatus 105 or particular aspects thereof. The infusion apparatus control application may operate to present an infusion apparatus user interface, such as the user interface 210 depicted in FIG. 2 and described in more detail below, on a display device 150. The infusion apparatus control application may receive information from the sensors 110. In one embodiment, the infusion apparatus control application may operate to display sensor 110 information on a user interface. In another embodiment, the infusion apparatus control application may analyze the sensor 110 information to determine one or more operating conditions of the infusion apparatus 105 and flow of fluids through the various fluid pathways 160, 165, 170, 175, 180, 185.

In one embodiment, the sensors 160 may comprise at least one radiation sensor positioned along the fluid pathways 160, 165, 170, 175, 180, 185. Non-limiting examples of sensors include silicon diodes, silicon PIN diode radiation sensors, avalanche diodes, scintillators, photomultipliers, solid state crystals, semiconductors, Geiger tubes, ionization-chamber radiation detectors, silicon photodiodes, microdischarge-based radiation detectors, sodium iodide crystal radiation detectors, bismuth tri-iodide crystal radiation detectors, or cadmium tellurium and cadmium zinc tellurium semiconductor crystal radiation detectors, and combinations thereof.

The processor 195 may receive information from the radiation sensors, which may be analyzed by the infusion apparatus control application. For example, the radiation sensor information may be analyzed to determine whether the radiopharmaceutical is traveling through the correct pathway. The infusion apparatus control application may be configured to expect radiation and/or certain levels of radiation at radiation sensors located at certain positions within the infusion apparatus 105. As such, if there is not an adequate radioactivity detected in radiopharmaceutical delivery paths 180 and 185 (and/or paths 170 and 175 if the dose meter 120 is being used) when the infusion apparatus 105 is infusing a patient with the radiopharmaceutical, this may indicate one or more fault conditions. For instance, it may indicate a leak, blockage, break, or other problem with the pathway, or that the pathway is not properly connected to the source container (e.g., 130). In another instance, inadequate radioactivity may indicate that the radiopharmaceutical container 130 does not have an adequate supply of the radiopharmaceutical. In a further instance, inadequate radioactivity may indicate that the infusion pump is not operating properly.

In the alternative, if the radioactivity in the radiopharmaceutical delivery paths (e.g., 180, 185 and/or 170, 175) is above an expected level, this may indicate one or more other fault conditions. Non-limiting examples of such fault conditions include an inadequate amount of saline, the directional valve being out of position, the saline is not properly diluting the radiopharmaceutical, and/or the radiopharmaceutical container 130 supplying radiopharmaceutical with an incorrect radioactivity level. In addition, radioactivity detected in an unexpected pathway, such as saline pathway 165, may indicate a general tubing leak.

The infusion apparatus control application may be configured to compare the level of radioactivity detected at the radiopharmaceutical source path 185 with the level of radioactivity detected at the delivery path 180. If the infusion protocol requires the radiopharmaceutical to be diluted with saline, then the radioactivity level at path 185 should be higher than the level at path 180 after the radiopharmaceutical has been diluted with saline. If the radioactivity level at path 180 is not lower by a threshold amount than the radioactivity level at path 185, the infusion apparatus control application may indicate a fault condition.

In another embodiment, the infusion apparatus control application may have values for the length of the various fluid pathways 160, 165, 170, 175, 180, 185 and combinations thereof and the expected infusion flow rate. The sensors 160 may comprise one or more sensors for detecting flow through the fluid pathways 160, 165, 170, 175, 180, 185 and combinations thereof. The infusion apparatus application may compare the flow rate received from the flow rate sensors and compare them with the expected flow rate. Discrepancies may be indicative of one or more fault conditions, such as a flow rate below a threshold value, a tubing leak, improper infusion pump operation, or detection of fluid in a dry pathway. For instance, saline may be used as a "chaser" to the radiopharmaceutical dispensed to the patient. A fault condition may occur if the detected level of flow in the saline 165 fluid pathway is below a threshold amount when the infusion apparatus 105 is supposed to be dispensing the saline to the patient.

According to some embodiments, the processor 195 may be communicatively coupled with one or more infusion apparatus 105 components, such as the infusion pump. In this manner, the infusion apparatus control application may use the component information to analyze sensor information indicating a fault condition. For instance, the infusion apparatus control application may check whether the infusion pump is working properly responsive to an indication of a low radioactivity condition. In another instance, the infusion apparatus control application may check the fluid level of saline in the medical fluid container 130 responsive to a fault condition indicating a high radioactivity condition to determine whether there is an adequate volume of saline to dilute the radiopharmaceutical. In a further instance, if the flow in the radiopharmaceutical delivery path is indicated as being low, the infusion apparatus control application may check whether the directional valve 140 is properly positioned to allow for the proper flow of the radiopharmaceutical and any other fluids (e.g., saline) required for a proper flow level.

The sensors 160 may comprise one or more optical sensors that may be used, among other things, for the presence of fluid in the fluid pathways 160, 165, 170, 175, 180, 185. Fluid fill detection may be used during certain steps in the infusion process, such as the dry tubing priming stage of the infusion process. The optical sensors may be used to detect fluid motion through dispersion or diffraction measurements across the tubing. The infusion apparatus control application may be configured to analyze information received from the optical sensors to make determinations about the presence of fluid. For instance, the detection of a fluid meniscus passing an optical detector may indicate the motion of fluid through a particular section of the fluid pathway 160, 165, 170, 175, 180, 185. In an embodiment, the infusion apparatus control application may be configured to determine if a bubble is in the fluid pathway 160, 165, 170, 175, 180, 185, for instance, as compared to a meniscus. In this embodiment, the detection of two menisci passing within a certain threshold time frame may be indicative of a bubble.

The infusion apparatus control application may be configured to analyze the fluid detection information to determine whether any fault conditions exist. For example, a fault condition may exist if fluid is detected in a section of the fluid pathway 160, 165, 170, 175, 180, 185 at an unexpected stage of the infusion process. Alternatively, a fault condition may be generated based on the absence of fluid in a section of the fluid pathway 160, 165, 170, 175, 180, 185 when required, such as the lack of radiopharmaceutical in the radiopharmaceutical source pathway 185 during the infusion process or a lack of saline in the saline pathway 165 when the infusion process requires dilution of the radiopharmaceutical.

Embodiments are not limited to the particular sensors and/or fault conditions described above as these are provided as illustrative and non-restrictive examples. Any sensor and/or fault condition capable of operating according to the described embodiments is contemplated herein.

As shown in FIG. 1, the infusion apparatus 105 may comprise one or more communication ports (not shown) that provide communication with a computing device 145 and/or networks 155. The communications ports may provide a connection to the computing device 145 or networks 155 through communication protocols known to those having ordinary skill in the art, such as serial, Ethernet and Wi-Fi connections. The communication ports may be the same or substantially similar to communications port 440 depicted in FIG. 4 and described below. According to some embodiments, the infusion apparatus user interface may be accessible through a display device 150 coupled to the computing device 145 or available through the network 155 (e.g., over the Internet and/or through a web application). The computing device 145 may comprise various types of computing devices, including, without limitation, a server, personal computer (PC), tablet computer, computing appliance, or smart phone device. Non-restrictive examples of networks 155 include communications networks or health information networks (e.g., picture archiving and communications system (PACS)). In this manner, information associated with and control of the infusion apparatus 105 may be accessible by systems remotely located from the infusion apparatus.

Figure 2:
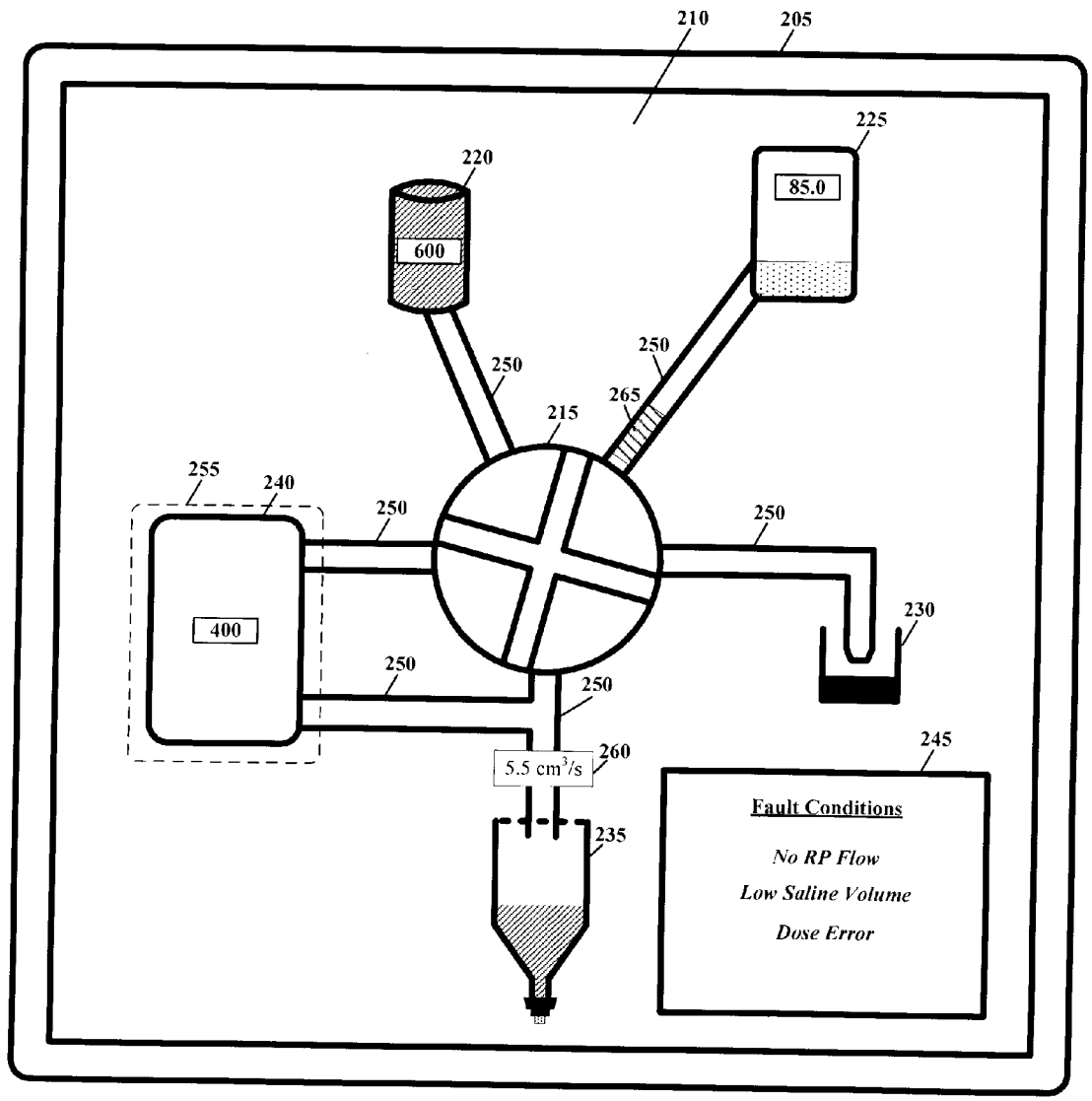
FIG. 2 depicts an illustrative infusion apparatus user interface according to some embodiments.

FIG. 2 depicts an illustrative infusion apparatus user interface according to some embodiments. As shown in FIG. 2, an infusion apparatus user interface ("user interface") 210 may comprise a dynamic graphical user interface (GUI) presented on a display device 205 (e.g., display monitor or touch screen device). As described above, the user interface 210 may be presented by an infusion device control application and may depict various components of the infusion apparatus. For instance, the user interface may present visual representations of the radiopharmaceutical source 220, the saline source 225, the dose meter 240, the waste container 230, the dispensing element 235, the directional valve 215, and the various fluid pathways 250.

The user interface 210 may be used to graphically represent information to an operator of an infusion apparatus. For example, the user interface 210 may indicate the status of infusion apparatus components, including, without limitation, the radiopharmaceutical source 220, the saline source 225, the dose meter 240, the waste container 230, the dispensing element 235, the directional valve 215, and the various fluid pathways 250 connecting the components. The status may be based on information transmitted from the components and/or the sensors (e.g., sensors 110 depicted in FIG. 1) to the processor (e.g., processor 195 depicted in FIG. 1). The transmitted information may be input into the infusion apparatus control application and analyzed to determine a status. For example, a dispensing element may provide a signal indicating whether it is active in dispensing a medical fluid to a patient. In another example, a saline source container may provide information of the amount of saline remaining in the container. In a further example, sensors configured to determine flow may provide information about the flow of fluid in a particular section of the fluid pathway.

Infusion apparatus information and component status may be represented in various forms through the user interface 210. For example, status and information may be represented by colors, flashing GUI elements, numerical elements, and text. Fluid flow may be indicated by a fluid flow GUI element 260. The sensors configured to detect and/or measure flow for a particular section of a flow pathway may transmit flow information to the infusion apparatus processor. The flow information may be analyzed by the infusion apparatus control application that is being executed by the infusion apparatus processor to generate flow information. The infusion apparatus control application may present the flow information in one or more various formats on the user interface 210 through one or more designated GUI elements (e.g., 260). In the illustrative embodiment depicted in FIG. 2, the flow information is displayed as a flow rate. However, embodiments provide that the flow information may be presented in various other formats, such as a flow/no flow indicator (e.g., one color for flow, another color for no flow through the section of the fluid pathway 250), or other real-time flow indicators. Information associated with other components may be similarly presented on the user interface 210.

In an embodiment, the position of the directional valve may be represented by a directional valve element 215 as well as the pathways connected through the directional valve may be indicated on the user interface 210. For example, connected pathways may be highlighted and similarly colored.

The user interface 210 may be configured to indicate fault conditions within the infusion apparatus. For example, components associated with a fault condition may be highlighted, such as with a flashing red boundary or enclosed within a GUI element indicating a fault condition. In FIG. 2, a dose meter fault condition GUI element 255 has been activated to indicate that there is a fault condition associated with the dose meter 240. A pathway or portions of a pathway may be highlighted to indicate a fault condition associated therewith, such as the highlighted region 265 depicted in FIG. 2. The fault condition associated with the highlighted region may indicate various conditions, including, without limitation, improper flow, a potential leak or improper connection, or radioactivity detected in an unexpected area. According to some embodiments, the fault conditions may be accompanied by other alert mechanisms, such as an audio alert or the transmission of messages (e.g., email, short message service (SMS), etc.) to one or more computing devices.

A message GUI element 245 may be presented on the user interface 210 to provide messages to operators of the infusion apparatus. For instance, the message GUI element 245 may be configured to present messages associated with the progress of the infusion process (e.g., infusion initiated, amount of dose administered, etc.). The message GUI element 245 may also be configured to present fault conditions and/or alarms as generated by the infusion apparatus control application based on information received from sensors and/or infusion apparatus components. The message GUI element 245 may operate in combination with other fault condition indicators presented on the user interface 210. For example, the dose meter fault condition GUI element 255 may indicate that there is a fault condition associated with the dose meter and descriptive text related to the fault condition, such as "low flow into dose meter," may be presented at the message GUI element 245.

The user interface 210 may provide functionality for a user to select a GUI component for more information or to perform a function. For example, a user may select the highlighted region 265 to receive information or functions related to the associated fault condition, such as through a window presented responsive to selection of the highlighted region. The information may comprise a more detailed assessment of the fault, while the functions may provide actions that may be taken in response to the fault condition (e.g., stop flow, stop infusion process, turn directional valve to close pathway, etc.). In an embodiment, the display device 205 may be a touch screen such that a user may select a component or fault by touching the associated area on the touch screen.

As depicted in FIG. 1, the infusion apparatus 105 may be communicatively connected with a computing device 145 and/or a network 155. The user interface 210 may be presented on one or more computing devices connected to the infusion apparatus directly or through a network 155. In an embodiment, the user interface 210 may be available as a web service, for example, as a web page available through the Internet. In another embodiment, multiple user interfaces 210 may be displayed simultaneously at a remote computing device, for example, at a central location of a healthcare facility having multiple infusion apparatuses. In this embodiment, a user may select to focus on one or more of the multiple user interfaces 210.

Figure 3:
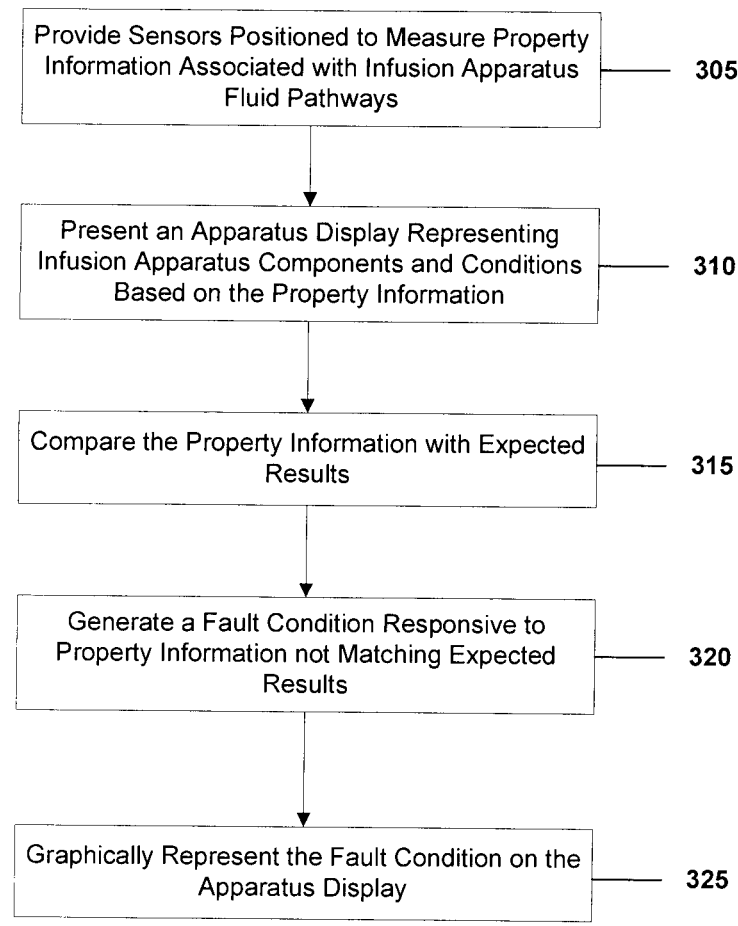
FIG. 3 depicts a flow diagram of a method of monitoring an automated radiopharmaceutical infusion apparatus according to an embodiment.

FIG. 3 depicts a flow diagram of a method of monitoring an automated radiopharmaceutical infusion apparatus according to an embodiment. As shown in FIG. 3, sensors may be provided 305 that are positioned to measure property information associated with infusion apparatus fluid pathways. The property information may comprise any information associated with the infusion apparatus fluid pathways, such as radioactivity, flow, temperature, and pressure. For example, radiation sensors may be positioned along each fluid pathway to measure radioactivity in and around the fluid pathway. In another example, sensors and/or combinations of sensors configured to measure the presence of fluid in a fluid pathway may be positioned within the infusion apparatus.

An apparatus display may be presented 310 that presents infusion apparatus components and conditions based on the property information. For example, a user interface may be presented on a display device that comprises GUI elements representing components of the infusion apparatus and information associated therewith. Each infusion apparatus component, including, without limitation, a dispensing element, a dose meter, at least one of the fluid pathways, a directional valve configured to connect at least two of the plurality of fluid pathways, and an infusion pump may be represented by a GUI element. According to some embodiments, each GUI element may be selected by a user (e.g., using a touch screen, mouse, stylus, keyboard, etc.) and the apparatus display may present operational information about the selected GUI element (e.g., operating conditions, fault conditions, etc.).

The property information may be compared 315 with expected results. For example, an infusion apparatus control application may be executed on a processor of the infusion apparatus. The infusion apparatus control application may be configured to maintain and/or calculate expected results for the property information. The processor may receive the property information and transmit it to the infusion apparatus control application for comparison with the expected results. For example, during an infusion process, the infusion apparatus control application may compare the flow of the radiopharmaceutical through a radiopharmaceutical dispensing pathway with the expected results. The infusion apparatus control application may be configured to compare any available property information and/or to make determinations based on the property information. For instance, the infusion apparatus control application may determine that there is a potential leak or defective connection in the saline line if there is no flow in the saline source pathway and the volume of saline in the saline container is above a specified threshold.

A fault condition may be generated 320 responsive to property information that does not match an expected result. For example, the infusion apparatus control application may trigger a fault condition if it receives property information that does not conform to an expected result. For example, the infusion apparatus control application may be configured to expect radioactivity in the saline source pathway to be below a certain threshold. If the property information for the saline source pathway indicates a level of radioactivity above the threshold, a fault condition may be triggered as this may indicate a fault within the infusion apparatus (e.g., a leak in the radiopharmaceutical source pathway). According to some embodiments, the comparisons may not be rigid; rather, certain of the comparisons may determine whether a measured property is within a specified range or above/below a threshold value.

The fault condition may be graphically represented 325 on the apparatus display. In this manner, an operator of the infusion apparatus may be alerted to potential fault conditions within the infusion apparatus. The fault condition may be represented as a text-based alarm and/or the components associated with the fault condition may be highlighted on the apparatus display. Representations of the fault condition are not limited to any particular forms, as embodiments provide that fault conditions may be represented in any manner capable of being graphically represented on the apparatus display.

FIG. 4 depicts a block diagram of exemplary internal hardware that may be used to contain or implement program instructions, such as the process steps discussed above in reference to FIG. 3, according to an embodiment. A bus 400 serves as the main information highway interconnecting the other illustrated components of the hardware. CPU 405 is the central processing unit of the system, performing calculations and logic operations required to execute a program. CPU 405, alone or in conjunction with one or more of the other elements disclosed in FIG. 1, is an exemplary processing device, computing device or processor as such terms are using in this disclosure. Read only memory (ROM) 410 and random access memory (RAM) 415 constitute exemplary memory devices.

A controller 420 interfaces with one or more optional memory devices 425 to the system bus 400. These memory devices 425 may include, for example, an external or internal DVD drive, a CD ROM drive, a hard drive, flash memory, a USB drive or the like. As indicated previously, these various drives and controllers are optional devices.

Program instructions, software or interactive modules for providing the digital marketplace and performing analysis on any received feedback may be stored in the ROM 410 and/or the RAM 415. Optionally, the program instructions may be stored on a tangible computer readable medium such as a compact disk, a digital disk, flash memory, a memory card, a USB drive, an optical disc storage medium, such as a Blu-Ray™ disc, and/or other recording medium.

An optional display interface 430 may permit information from the bus 400 to be displayed on the display 435 in audio, visual, graphic or alphanumeric format. Communication with external devices may occur using various communication ports 440. An exemplary communication port 440 may be attached to a communications network, such as the Internet or an intranet. Other exemplary communication ports 440 may comprise a serial port, a RS-232 port, and a RS-485 port.

The hardware may also include an interface 445 which allows for receipt of data from input devices such as a keyboard 450 or other input device 455 such as a mouse, a joystick, a touch screen, a remote control, a pointing device, a video input device, and/or an audio input device.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A system for monitoring an automated radiopharmaceutical infusion apparatus, the system comprising:
   a plurality of fluid pathways comprising a radiopharmaceutical source pathway and a radiopharmaceutical delivery pathway;
   a plurality of sensors, each of which is positioned to measure at least one property associated with one of the plurality of fluid pathways, wherein at least one of the plurality of sensors is positioned to measure a level of radioactivity of a fluid in the radiopharmaceutical source pathway and at least one of the plurality of sensors is positioned to measure a level of radioactivity of a fluid in the radiopharmaceutical delivery pathway at a point after which saline is expected to have been added to the fluid in the radiopharmaceutical delivery pathway;
   a display device;
   a processor in communication with the plurality of sensors and the display device; and
   a non-transitory, computer-readable storage medium in operable communication with the processor, wherein the computer-readable storage medium contains one or more programming instructions that, when executed, cause the processor to:
      receive property information, including at least the level of radioactivity of the fluid in each of the radiopharmaceutical source pathway and the radiopharmaceutical delivery pathway, from the plurality of sensors,
      present an apparatus display graphically representing apparatus components based on the property information, including at least the level of radioactivity of the fluid in each of the radiopharmaceutical source pathway and the radiopharmaceutical delivery pathway, on the display device,
      compare the property information, including at least the level of radioactivity of the fluid in each of the radiopharmaceutical source pathway and the radiopharmaceutical delivery pathway, with expected results, wherein comparing the property information with the expected results comprises determining a difference between the level of radioactivity of the fluid in the radiopharmaceutical source pathway and the level of radioactivity of the fluid in the radiopharmaceutical delivery pathway,
      generate a fault condition, when the system is infusing a patient with a radiopharmaceutical, responsive to the difference between the level of radioactivity of the fluid in the radiopharmaceutical source pathway and the level of radioactivity of the fluid in the radiopharmaceutical delivery pathway not matching the expected results, and
      graphically represent the fault condition on the apparatus display.

2. The system of claim 1, wherein the plurality of fluid pathways further comprise at least one of a saline pathway, a dose meter inlet pathway, a dose meter outlet pathway, and a waste pathway.

3. The system of claim 1, wherein at least one of the plurality of sensors comprises at least one of a silicon diode, a silicon PIN diode, an avalanche diode, a scintillator, a photomultiplier, a solid state crystal, a semiconductor, Geiger tubes, an ionization-chamber, a silicon photodiode, a microdischarge-based sensor, a sodium iodide crystal sensor, a bismuth tri-iodide crystal sensor, a cadmium tellurium crystal sensor, a cadmium zinc tellurium semiconductor sensor, and combinations thereof.

4. The system of claim 1, comprising at least one of a temperature sensor, a pressure sensor, an optical sensor, an analyte sensor, a concentration sensor, a flow sensor, an electro-resistive device, an electro-capacitive device, and an ultrasound device.

5. The system of claim 1, wherein the plurality of fluid pathways comprises at least one of a dose meter outlet pathway and a waste pathway, and wherein at least one of the plurality of sensors is associated with one of the dose meter outlet pathway and the waste pathway.

6. The system of claim 5, wherein the property information received from the plurality of sensors comprises the level of radioactivity from the at least one of the plurality of sensors associated with at least one of the dose meter outlet pathway and the waste pathway.

7. The system of claim 1, further comprising a communication port configured to provide wireless communication between one or, more of the infusion apparatus, the plurality of sensors, the processor, the display device, and a network.

8. The system of claim 7, wherein the display device comprises one or more of a server, a personal computer, a tablet computer, a computing appliance, and a smart phone device, and wherein the network comprises one or more of a communications network, a health information network, and a picture archiving and communications system network.

9. The system of claim 7, wherein the communication port is configured to provide wireless communication over a Wi-Fi connection.

10. A method for monitoring an automated radiopharmaceutical infusion apparatus, the method comprising:
 providing a plurality of sensors positioned to measure at least one property associated with a plurality of fluid pathways comprising a radiopharmaceutical source pathway and a radiopharmaceutical delivery pathway, wherein at least one of the of the plurality of sensors is positioned to measure a level of radioactivity of a fluid in the radiopharmaceutical source pathway and at least one of the of the plurality of sensors is positioned to measure a level of radioactivity of a fluid in the radiopharmaceutical delivery pathway at a point after which saline is expected to have been added to the fluid in the radiopharmaceutical delivery pathway;
 providing a processor operatively connected to a display device and the plurality of sensors; and
 causing the processor to enable monitoring of the automated radiopharmaceutical infusion apparatus, wherein monitoring of the apparatus comprises:
  receiving property information including at least the level of radioactivity of the fluid in each of the radiopharmaceutical source pathway and the radiopharmaceutical delivery pathway, from the plurality of sensors,
  presenting an apparatus display graphically representing apparatus components based on the property information including at least the level of radioactivity of the fluid in each of the radiopharmaceutical source pathway and the radiopharmaceutical delivery pathway, on the display device,
  comparing the property information including at least the level of radioactivity of the fluid in each of the radiopharmaceutical source pathway and the radiopharmaceutical delivery pathway with expected results, wherein comparing the property information with the expected results comprises determining a difference between the level of radioactivity of the fluid in the radiopharmaceutical source pathway and the level of radioactivity of the fluid in the radiopharmaceutical delivery pathway,
  generating a fault condition, when the automated radiopharmaceutical infusion apparatus is infusing a patient with a radiopharmaceutical, responsive to the difference between the level of radioactivity of the fluid in the radiopharmaceutical source pathway and the level of radioactivity of the fluid in the radiopharmaceutical delivery pathway not matching the expected results, and
  graphically representing the fault condition on the apparatus display.

11. The method of claim 10, wherein monitoring of the apparatus further comprises receiving, with the processor, a signal of a selection by a user of one or more of the apparatus components.

12. The method of claim 10, wherein monitoring of the apparatus further comprises receiving, with the processor, a signal of a selection by a user of the graphically represented fault condition.

13. The method of claim 10, wherein monitoring of the apparatus further comprises presenting, by the processor, at least one function for managing the graphically represented fault condition.

14. The method of claim 13, wherein the at least one function comprises at least one of stopping infusion and closing at least one of the plurality of fluid pathways.

15. The method of claim 10, further comprising, providing at least one of a temperature sensor, a pressure sensor, an optical sensor, an analyte sensor, a concentration sensor, a flow sensor, an electro-resistive device, an electro-capacitive device, and an ultrasound device.

16. The method of claim 10, wherein the apparatus components comprise at least one fluid pathway.

17. The method of claim 10, wherein the apparatus components comprise a directional valve configured to connect at least two of the plurality of fluid pathways.

18. The method of claim 10, wherein the fault condition comprises the difference between the level of radioactivity of the fluid in the radiopharmaceutical source pathway and the level of radioactivity of the fluid in the radiopharmaceutical delivery pathway being above a threshold value.

19. The method of claim 10, wherein the plurality of fluid pathways comprises at least one of a dose meter outlet pathway and a waste pathway, and wherein at least one of the plurality of sensors is associated with one of the dose meter outlet pathway and the waste pathway.

20. The method of claim 19, wherein the property information received from the plurality of sensors comprises the level of radioactivity from the at least one of the plurality of sensors associated with at least one of the dose meter outlet pathway and the waste pathway.

21. The method of claim 10, wherein providing the processor operatively connected to the display device and the plurality of sensors comprises providing a processor that is wirelessly connected to one of the display device and the plurality of sensors.

22. The method of claim 21, wherein presenting an apparatus display graphically representing apparatus components on the display device comprises wirelessly transmitting the apparatus display from the processor to the display device via a communication port, and wherein graphically representing the fault condition on the apparatus display comprises wirelessly transmitting the fault condition from the processor to the display device via the communication port,
 wherein the communication port is configured to provide wireless communication over a Wi-Fi connection.

23. The method of claim 21, wherein one or more of the apparatus display and the fault condition are wirelessly transmitted to an external computer network via a communication port, the external computer network being one or more of a communications network, a health information network and a picture archiving and communications system network, and
 wherein the communication port is configured to provide wireless communication over a Wi-Fi connection.

* * * * *

UNITED STATES PATENT AND TRADEMARK OFFICE
CERTIFICATE OF CORRECTION

| | | |
|---|---|---|
| PATENT NO. | : 9,757,591 B2 | Page 1 of 1 |
| APPLICATION NO. | : 13/764426 | |
| DATED | : September 12, 2017 | |
| INVENTOR(S) | : Agamaite et al. | |

It is certified that error appears in the above-identified patent and that said Letters Patent is hereby corrected as shown below:

In the Specification

In Column 10, Line 41, delete "130, 130." and insert -- 130, 135. --, therefor.

In Column 11, Line 40, delete "sensors 160" and insert -- sensors 110 --, therefor.

In Column 12, Line 34, delete "sensors 160" and insert -- sensors 110 --, therefor.

In Column 12, Line 58, delete "medical fluid container 130" and insert -- medical fluid container 115 --, therefor.

In Column 13, Line 1, delete "sensors 160" and insert -- sensors 110 --, therefor.

In the Claims

In Column 18, Line 66, in Claim 7, delete "one or," and insert -- one or --, therefor.

In Column 19, Line 16, in Claim 10, delete "of the of the" and insert -- of the --, therefor.

In Column 19, Line 19, in Claim 10, delete "of the of the" and insert -- of the --, therefor.

Signed and Sealed this
Thirteenth Day of March, 2018

Andrei Iancu
*Director of the United States Patent and Trademark Office*